(12) United States Patent
Chen

(10) Patent No.: US 10,993,475 B2
(45) Date of Patent: May 4, 2021

(54) ELECTRONIC CIGARETTE AND ATOMIZER THEREOF

(71) Applicant: Shenzhen Smoore Technology Limited, Shenzhen (CN)

(72) Inventor: Zhiping Chen, Shenzhen (CN)

(73) Assignee: Shenzhen Smoore Technology Limited, Shenzhen (CN)

( * ) Notice: Subject to any disclaimer, the term of this patent is extended or adjusted under 35 U.S.C. 154(b) by 422 days.

(21) Appl. No.: 15/762,402

(22) PCT Filed: Aug. 5, 2016

(86) PCT No.: PCT/CN2016/093522
§ 371 (c)(1),
(2) Date: Mar. 22, 2018

(87) PCT Pub. No.: WO2017/067278
PCT Pub. Date: Apr. 27, 2017

(65) Prior Publication Data
US 2018/0289058 A1    Oct. 11, 2018

(30) Foreign Application Priority Data

Oct. 22, 2015  (CN) .......................... 201510690956.3
Nov. 27, 2015  (CN) .......................... 201510854348.1

(51) Int. Cl.
*A24F 13/00*  (2006.01)
*A24F 47/00*  (2020.01)
(Continued)

(52) U.S. Cl.
CPC .............. *A24F 47/008* (2013.01); *A24F 7/00* (2013.01); *A24F 40/44* (2020.01); *F16J 15/021* (2013.01);
(Continued)

(58) Field of Classification Search
CPC ...................................................... A24F 47/00
(Continued)

(56) References Cited

U.S. PATENT DOCUMENTS 10,226,076 B2 *  3/2019  Althorpe ................. A24F 40/40
2014/0299125 A1  10/2014  Buchberger
2016/0135505 A1 *  5/2016  Li ......................... A24F 47/008
131/329

FOREIGN PATENT DOCUMENTS

CN    201938355 U    8/2011
CN    203435687 U    2/2014
(Continued)

OTHER PUBLICATIONS

European Office Action, Issued in Application No. EP 16856713.9, dated Sep. 24, 2018 (7 pages).
(Continued)

*Primary Examiner* — Phuong K Dinh
(74) *Attorney, Agent, or Firm* — Coats & Bennett, PLLC

(57) ABSTRACT

An atomizer includes a main body defining an airflow channel and a liquid storage cavity isolated from each other and an atomizing element. The atomizing element includes a porous body and a porous heating film. The porous body includes an atomizing surface and a liquid absorption surface. The atomizing surface is a plane and is substantially parallel to a direction of an air flow in the airflow channel, (Continued)

and the porous heating film is formed on the atomizing surface. The liquid absorption surface can absorb a liquid in the liquid storage cavity.

19 Claims, 9 Drawing Sheets

(51) Int. Cl.
  *H05B 3/44* (2006.01)
  *A24F 40/44* (2020.01)
  *F16J 15/02* (2006.01)
  *H05B 3/12* (2006.01)
  *A24F 7/00* (2006.01)
  *A24F 40/46* (2020.01)

(52) U.S. Cl.
  CPC ................ *H05B 3/12* (2013.01); *H05B 3/44* (2013.01); *A24F 40/46* (2020.01); *H05B 2203/013* (2013.01); *H05B 2203/017* (2013.01); *H05B 2203/021* (2013.01); *H05B 2203/022* (2013.01)

(58) Field of Classification Search
  USPC .................................................. 131/328–329
  See application file for complete search history.

(56) References Cited

FOREIGN PATENT DOCUMENTS

| | | |
|---|---|---|
| CN | 203467677 U | 3/2014 |
| CN | 203523811 U | 4/2014 |
| CN | 103932401 A | 7/2014 |
| CN | 103960782 A | 8/2014 |
| CN | 203776165 U | 8/2014 |
| CN | 203952431 U | 11/2014 |
| CN | 104522891 A | 4/2015 |
| CN | 204317489 U | 5/2015 |
| CN | 104824853 A | 8/2015 |
| CN | 104983079 A | 10/2015 |
| CN | 105394816 A | 3/2016 |
| CN | 105693287 A | 6/2016 |
| WO | 2014198157 A1 | 12/2014 |
| WO | 2015077645 A1 | 5/2015 |
| WO | 2015114327 A1 | 8/2015 |
| WO | 2015114328 A1 | 8/2015 |

OTHER PUBLICATIONS

EP Search Report dated Mar. 13, 2019 in re EP Application No. 18207525 filed Dec. 23, 2015.

* cited by examiner

ELECTRONIC CIGARETTE AND ATOMIZER THEREOF

CROSS-REFERENCE TO RELATED APPLICATION

This application claims the benefit of Chinese Patent Application No. 201510690956.3, entitled "ELECTRONIC CIGARETTE, ATOMIZING COMPONENT AND ATOMIZING ELEMENT THEREOF", filed on Oct. 22, 2015, and claims the benefit of Chinese Patent Application No. 201510854348.1, entitled "ELECTRONIC CIGARETTE, ATOMIZING COMPONENT AND ATOMIZING ELEMENT THEREOF", filed on Nov. 27, 2015, and which are incorporated herein by reference in their entireties.

TECHNICAL FIELD

The present disclosure relates to the technical field of smoking device, particularly relates to an electronic cigarette and an atomizer thereof.

BACKGROUND

An electronic cigarette is also known as a virtual cigarette, or an electronic atomizer. An electronic cigarette has the similar appearance and taste of cigarette, but generally does not contain harmful ingredients, such as tar and particulate matter.

An atomizing component is a key device of the electronic cigarette to generated atomized gases, its atomizing effect determines the quality and taste of the smoke. A conventional atomizing component has a spiral heating wire as a heater, and the heating wire twines on a liquid absorption core. When the heating wire is electrified, the liquid stored in the liquid absorption core is atomized via the effect of heating wire, so as to generate the smoke.

However, according to the previously described electronic cigarette, since the heating wire is of a linear shape, only the liquid near the heating wire is heated and atomized, the liquid away from the heating wire and in the gaps of the spiral heating wire can hardly be atomized. Additionally, as the distance from the heating wire increases, the temperature decreases drastically, therefore, the atomizing temperature of the liquid is not uniform, resulting in different sizes of the atomized particles of the liquid, and a poor atomizing effect.

SUMMARY

Accordingly, it is necessary to provide an electronic cigarette and an atomizer thereof with a better atomizing effect.

An atomizer of an electronic cigarette includes:

a main body defining an airflow channel and a liquid storage cavity isolated from each other therein; and an atomizing element comprising a porous body and a porous heating film; the porous body comprising an atomizing surface and a liquid absorption surface; the atomizing surface being a plane substantially parallel to a direction of an airflow in the airflow channel, the porous heating film being formed on the atomizing surface and being capable of absorbing liquid in the liquid storage cavity.

An electronic cigarette includes a battery device and the previously described atomizer, the battery device is electrically coupled to the atomizer and is configured to power the atomizer.

According to the previously described electronic cigarette and atomizer thereof, the porous body can not only block the liquid, but ensure a liquid conduction effect. The porous heating film is configured to atomize the liquid in the porous body, and the micropores on the porous heating film can significantly increase a contacting area of liquid, thus the atomizing efficiency is improved. The porous heating film is located on the atomizing surface of the porous body, facilitates the atomized liquid to escape form the porous body. The atomizing surface is a plane, which facilitates the formation of an uniform porous heating film. The porous heating film can uniformly heats the surface of the porous body, therefore, the temperature of atomizing effect is uniform, which ensures that the atomized particles are uniform without relatively larger atomized particles caused by partial low temperature. The atomizing surface is substantially parallel to a direction of an air flow in the airflow channel, thus the air flow can easily passes over the atomizing surface and takes away the atomized liquid. The previously described electronic cigarette and atomizer thereof can perform a good atomizing effect and improve the taste of the electronic cigarette.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

FIG. 2 is a cross-sectional view taken along line II-II of FIG. 1a;

DETAILED DESCRIPTION OF THE EMBODIMENTS

Embodiments of the present disclosure are described more fully hereinafter with reference to the accompanying drawings. A preferred embodiment is described in the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Unless otherwise defined, all terms (including technical and scientific terms) used herein have the same meaning as commonly understood by one of ordinary skill in the art to which this present disclosure belongs. It will be further understood that the terms used herein the specification are for the purpose of describe detailed embodiments only, and are not intended to limit the present disclosure. As used herein, the term "and/or" includes any and all combinations of one or more of the associated listed items.

Figure 1:
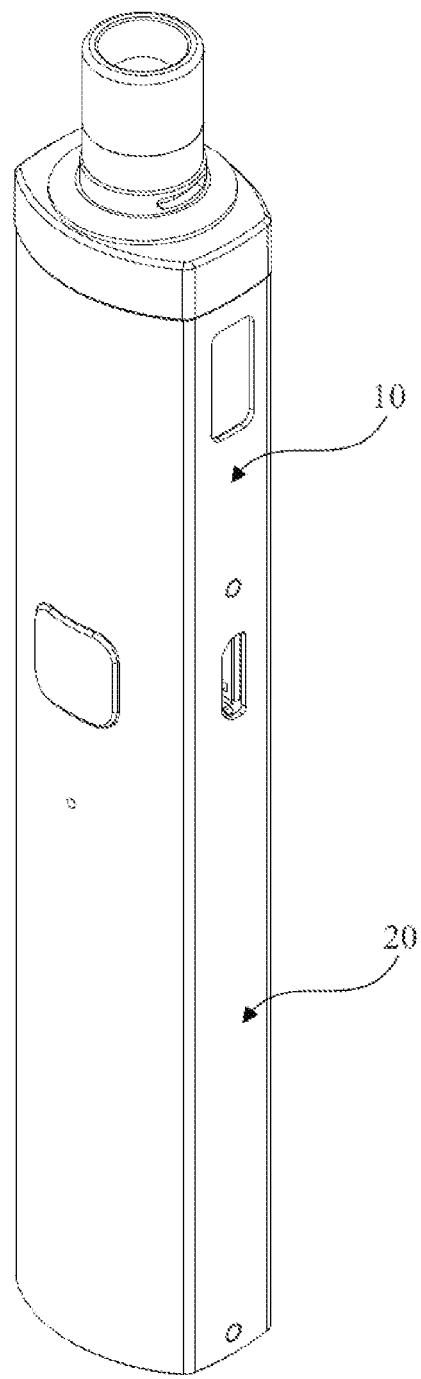
FIG. 1 is a perspective view of an electronic cigarette according to an embodiment.
Figure 1A:
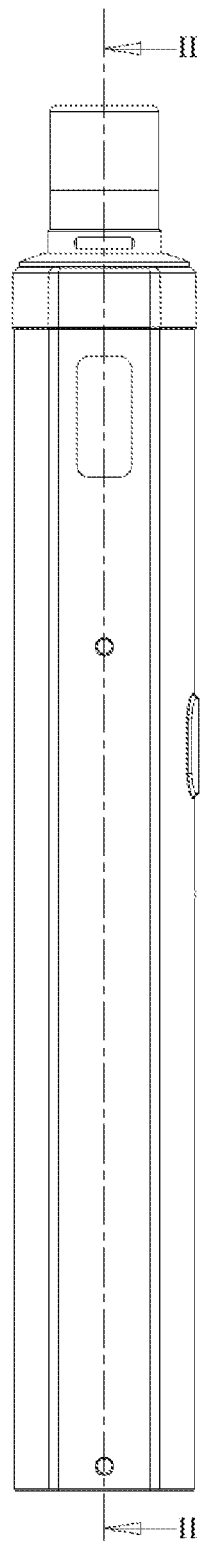
FIG. 1a is a right side elevational view of the electronic cigarette of FIG. 1.
Figure 1B:
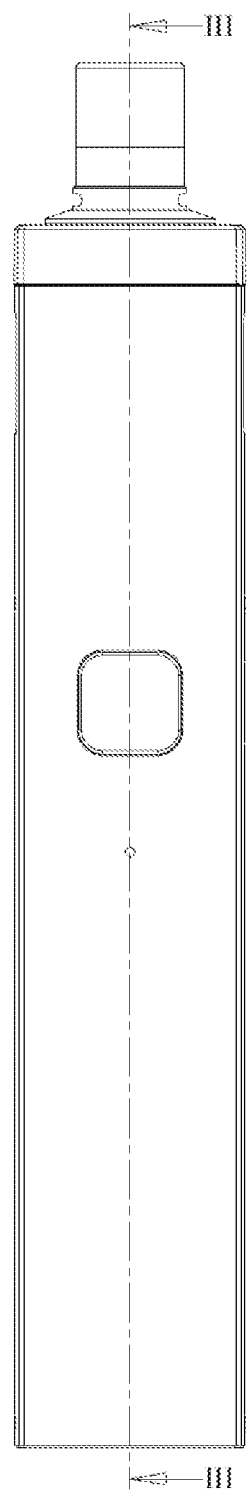
FIG. 1b is a front elevational view of the electronic cigarette of FIG. 1.
Figure 2:
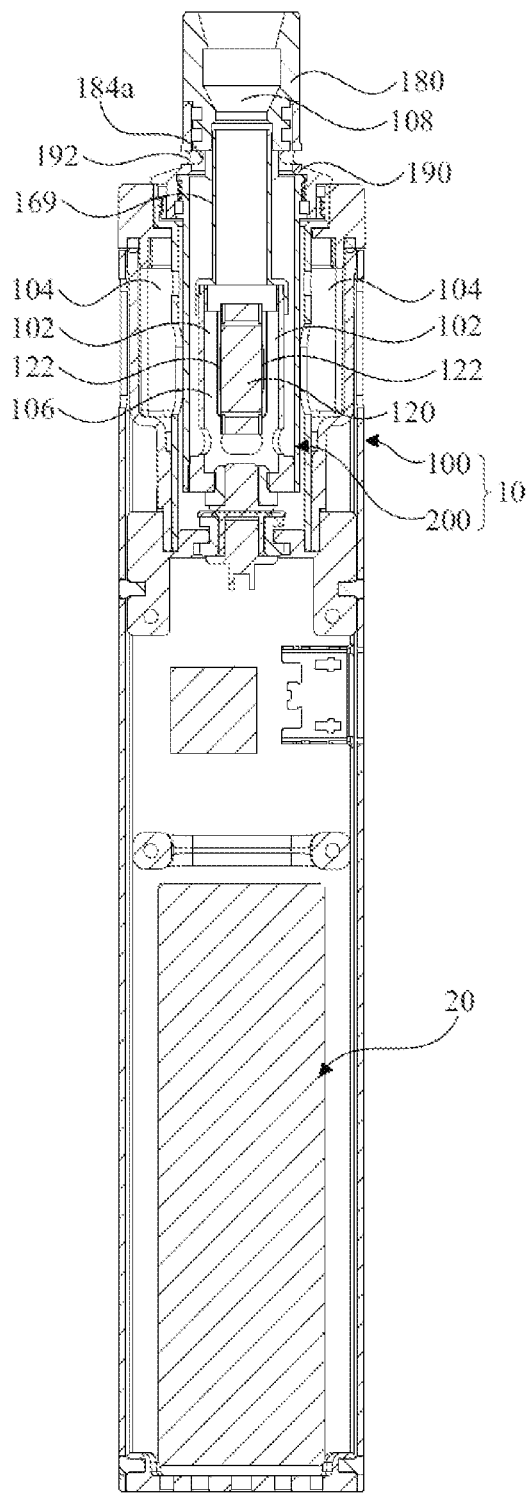
Figure 3:
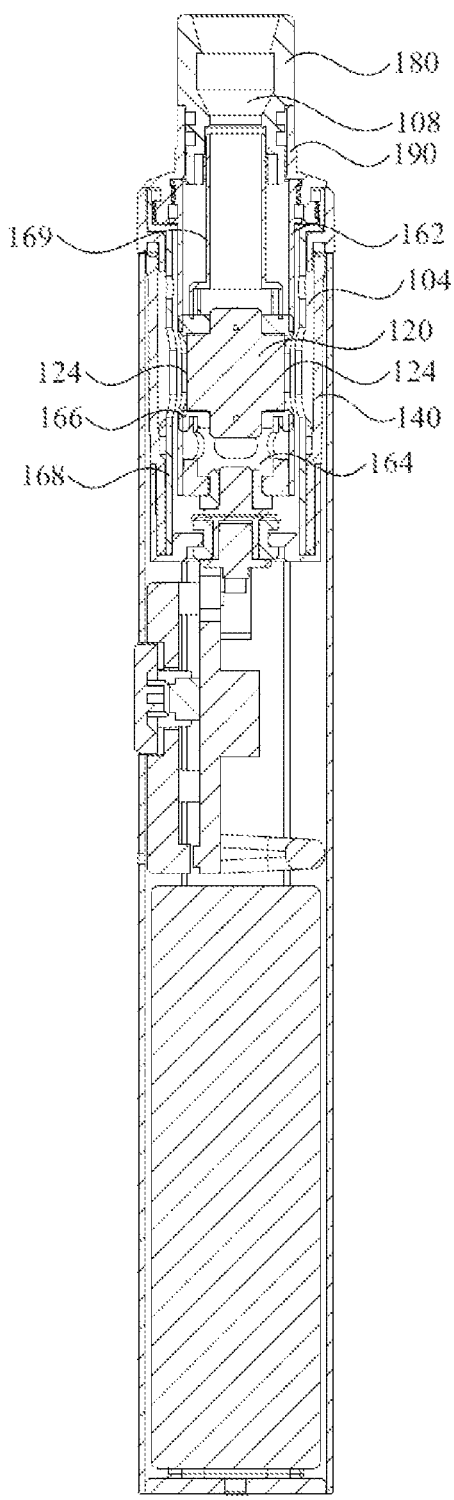
FIG. 3 is a cross-sectional view taken along line III-III of FIG. 1b.
Figure 4:
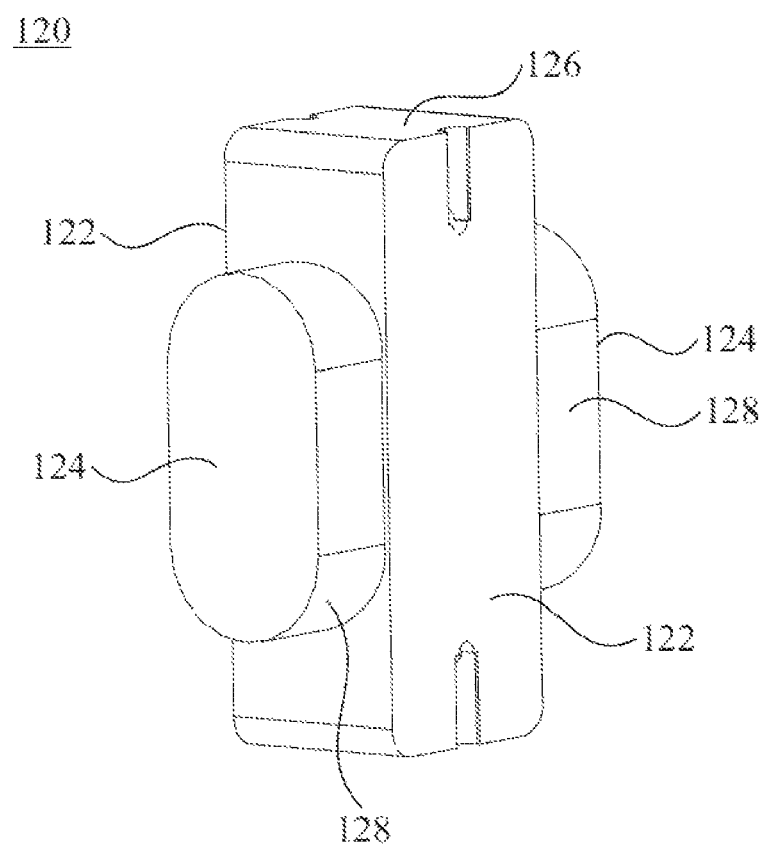
FIG. 4 is a perspective view of an atomizing element of the electronic cigarette of FIG. 1.

Referring to FIG. 1 and FIG. 2, an electronic cigarette according to an embodiment includes a atomizer 10 and a battery device 20, the battery device 20 is electrically coupled to the atomizer 10 and is configured to power the atomizer 10. The atomizer 10 includes a main body 100 and an atomizing element 200. The main body 100 defines an airflow channel 102 and a liquid storage cavity 104 therein to store liquid, and the airflow channel 102 and the liquid storage cavity 104 are isolated from each other. Referring to FIG. 3 and FIG. 4, the atomizing element 200 includes a porous body 120 and a porous heating film (not shown). The porous body 120 includes an atomizing surface 122 and a liquid absorption surface 124. The atomizing surface 122 is a plane and is substantially parallel to a direction of an air flow in the airflow channel 102, and the porous heating film is formed on the atomizing surface 122. The liquid absorption surface 124 can absorb the liquid in the liquid storage cavity 104. Specifically, in an embodiment, the number of the atomizing surfaces 122 is two, and the two atomizing surfaces 122 are oppositely arranged, and/or the number of the liquid absorption surfaces 124 is two, and the two liquid absorption surfaces 124 are oppositely arranged. The two opposite atomizing surfaces 122 and liquid absorption surfaces 124 can improve the efficiency of atomizing and liquid absorption.

The porous body 120 can not only block the liquid, but also ensure the liquid conduction effect. The porous heating film is configured to atomize the liquid in the porous body 120, and the micropores on the porous heating film can significantly increase a contacting area with the liquid, thus the atomizing efficiency is improved. The porous heating film is located on the atomizing surface 122 of the porous body 120, which can facilitate the atomized liquid to escape from the porous body 120. The atomizing surface 122 is a plane, which facilitates the formation of a uniform porous heating film. The porous heating film allows the surface of the porous body 120 to be uniformly heated, therefore, the temperature of atomizing effect is uniform, which ensures that the atomized particles are uniform without relatively larger atomized particles caused by partial low temperature. The atomizing surface 122 is substantially parallel to a direction of an air flow in the airflow channel 102, thus the air flow can easily pass over the atomizing surface 122 and take away the atomized liquid. The previously described electronic cigarette and atomizer 10 thereof can perform an excellent atomizing effect and improve the taste of the electronic cigarette.

Figure 5:
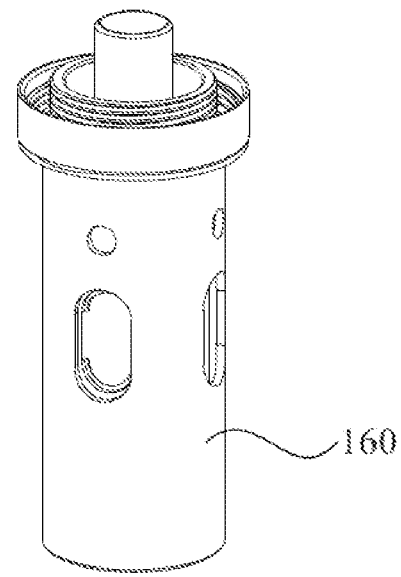
FIG. 5 is a perspective view of a liquid reservoir and an atomizing core of the electronic cigarette of FIG. 1.
Figure 5:
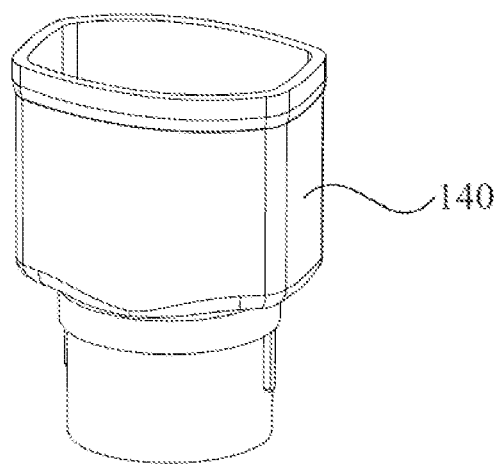

Referring to FIG. 3 and FIG. 5, in an embodiment, the main body 100 includes a liquid reservoir 140 and an atomizing core 160. The liquid storage cavity 104 is located in the liquid reservoir 140, and the atomizing core 160 is located in the liquid storage cavity 104. The atomizing element 200 and the airflow channel 102 are both located in the atomizing core 160, the atomizing core 160 defines a connecting hole, and the liquid absorption surface 124 is located on the connecting hole, and absorbs the liquid in the liquid storage cavity 104 via the connecting hole.

Figure 6:
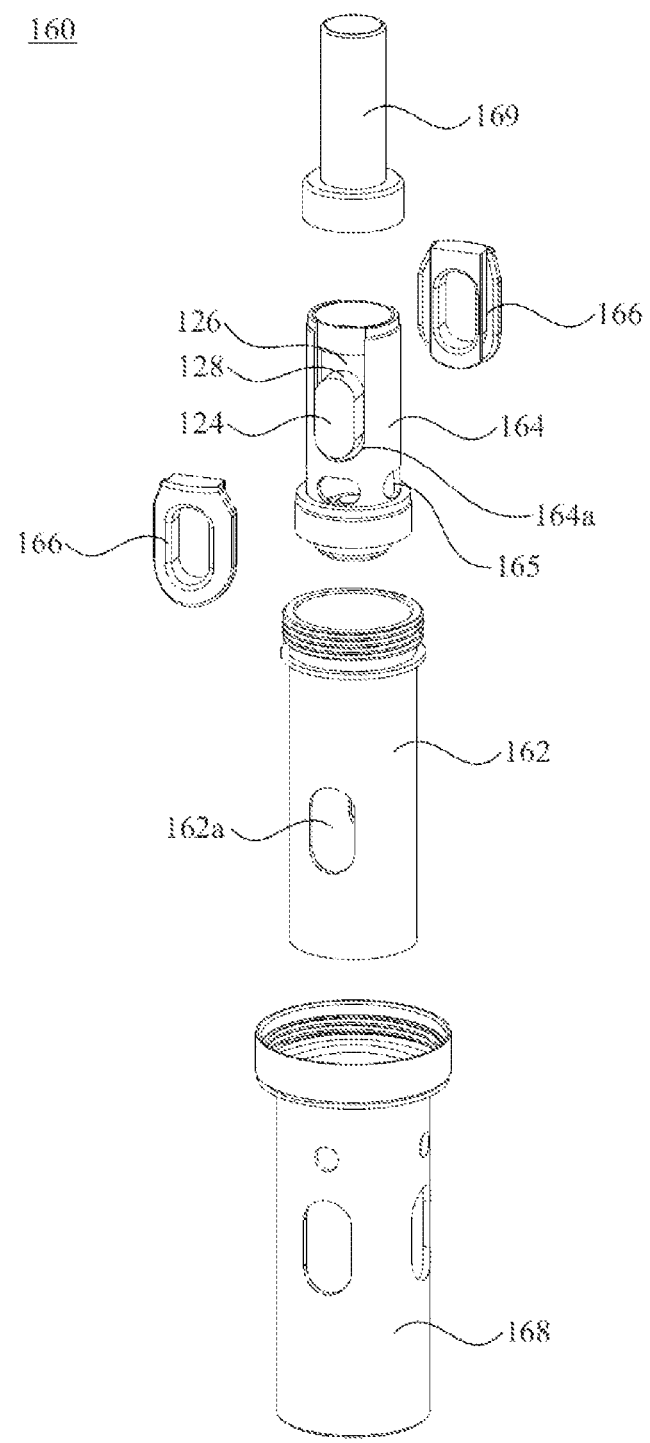
FIG. 6 is an perspective, exploded view of the atomizing core of the electronic cigarette in FIG. 1.

Referring to FIG. 2 and FIG. 6, further in an embodiment, the atomizing core 160 includes an outer tube 162, an inner tube 164, and a sealing gasket 166. The outer tube 162 is sleeved on the inner tube 164, and an intake channel 106 is formed between the outer tube 162 and the inner tube 164. The atomizing element 200 and the airflow channel 102 are both located in the inner tube 164. The intake channel 106 is in communication with an end of the airflow channel 102. Specifically, in an embodiment, a hole 165 for venting can be defined on the inner tube 164, so that the intake channel 106 is in communication with the airflow channel 102. The outer tube 162, the inner tube 164, and the atomizing element 200 are sleeved on each other to form the intake channel 106 and the airflow channel 102, so as to facilitate the production and reduce the cost.

The connecting hole includes a first connecting hole 162a and a second connecting hole 164a. The first connecting hole 162a is located in the outer tube 162, the second connecting hole 164a is located in the inner tube 164. The first connecting hole 162a is corresponding to the second connecting hole 164a. The sealing gasket 166 is located between the inner tube 164 and the outer tube 162, and the sealing gasket 166 surrounds the first connecting hole 162a and/or the second connecting hole 164a, such that the intake channel 106 is isolated from the first connecting hole 162a and the second connecting hole 164a. Meanwhile, since the sealing gasket 166 has some flexibility, the connection between the inner tube 164 and the outer tube 162 is more reliable. The sealing gasket 166 can be made of rubber or silicon, which can provide a better sealing effect.

Referring to FIG. 4 and FIG. 6, in an embodiment, the porous body 120 includes a integrally connected main part 126 and a protruding portion 128. The atomizing surface 122 is located on the main part 126, the liquid absorption surface 124 is located on the protruding portion 128, and the liquid absorption surface 124 is relatively distant from the main part 126. A side wall of the inner tube 164 defines a latching groove 164b, the protruding portion 128 is latched into the latching groove 164b, and the sealing gasket 166 surrounds the protruding portion 128. During assembling the porous body 120, the protruding portion 128 is directly latched into the latching groove 164b, and the connecting hole is simultaneously formed, so as to facilitate the assembling and simplify the manufacturing process.

Figure 7:
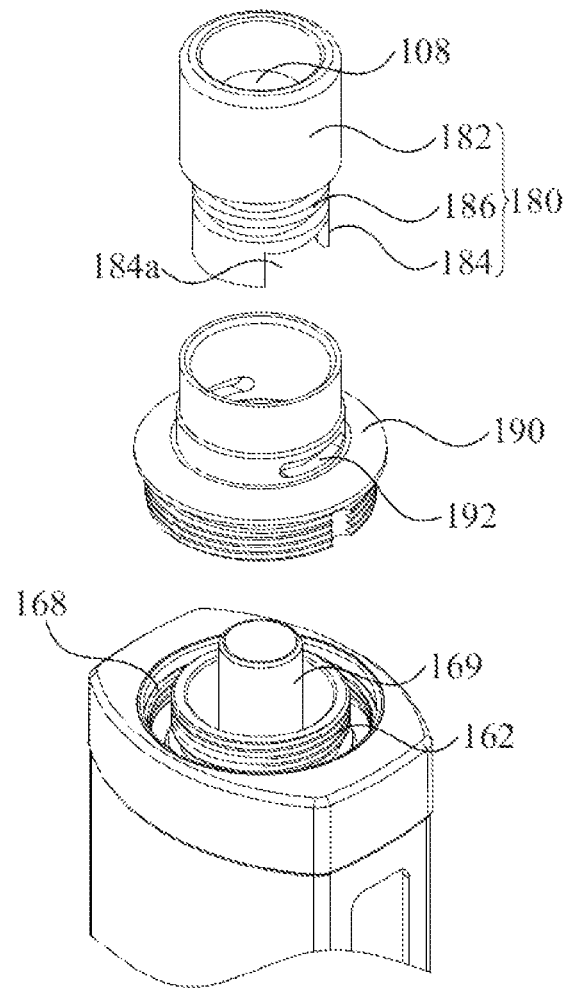
FIG. 7 is a perspective of a mouthpiece and a connecting sleeve of the electronic cigarette of FIG. 1.

Referring to FIG. 2 and FIG. 7, in an embodiment, the main body 100 further includes a mouthpiece 180 and a connecting sleeve 190. The mouthpiece 180 includes a mouth portion 182 and a shielding portion 184, and the mouth portion 182 defines an outlet channel 108, which is in communication with the other end of the airflow channel 102. The shielding portion 184 is fixed to the mouth portion 182, and the shielding portion 184 defines an adjusting opening 184a. The connecting sleeve 190 is connected to the outer tube 162 and sleeved on the mouthpiece 180, and the connecting sleeve 190 is rotatably connected to the mouthpiece 180. The connecting sleeve 190 defines an air inlet 192 in communication with the intake channel 106, the shielding portion 184 can cover the air inlet 192, and the adjusting opening 184a corresponds to the air inlet 192, a coincident area of the adjusting opening 184a and the air inlet 192 can be adjusted by rotating the mouthpiece 180.

The electronic cigarette according to the illustrated embodiment can adjust the amount of air flow via rotating the mouthpiece 180. Specifically, the shielding portion 184 can cover the air inlet 192, the adjusting opening 184a corresponds to the inlet 192. Rotating the mouthpiece 180 can thus adjust the coincident area of the adjusting opening 184a and the air inlet 192, so as to adjust the amount of the air flow. Since the air flow is adjusted via rotating the mouthpiece 180, a rotating ring of a conventional air flow adjusting component can be omitted, thus the structure of the electronic cigarette is simplified and the cost is reduced.

Specifically, in an embodiment, the air inlet 192 is an elongated hole extending along a circumferential direction of the connecting sleeve 190, so as to increase a range of the amount of air flow adjusted by rotating the mouthpiece 180. In an embodiment, the adjusting opening 184a is a notch defined on an edge of the shielding portion 184 away from the mouth portion 182, thus the structure is further simplified to facilitate the manufacturing process and reduce the cost.

The mouthpiece 180 further includes a connecting portion 186 located between the mouth portion 182 and the shielding portion 184, the connecting sleeve 190 is sleeved on the connecting portion 186, and the mouthpiece 180 is rotatably connected to the connecting sleeve 190 via the connecting portion 186. Referring to FIG. 6, in an embodiment, the atomizing core 160 further includes a connecting tube 168 sleeved on the outer tube 162, one end of the connecting tube 168 is connected to the liquid reservoir 140, and the other end of the connecting tube 168 is connected to the connecting sleeve 190. In an embodiment, the atomizing core 160 further includes an air tube 169, one end of the air tube 169 is connected to the inner tube 164, and the other end of the air tube 169 is connected to the mouthpiece 180. The connecting tube 168 and the air tube 169 can facilitate the manufacturing and assembly process, and can also improve the reliability of connecting.

Referring to FIG. 3, in an embodiment, a diameter of a micropore on the porous heating film is less than a diameter of a micropore on the porous body 120. The atomizing surface 122 of the electronic cigarette is located in the airflow channel 102, the porous body 120 is directly exposed to air. Since the porous body 120 has micropores with larger diameters, and the liquid is easier to be leaked during the storage of electronic cigarette. In the illustrated embodiment, since the porous heating film formed on the porous body 120 has less pore diameters, the leakage of liquid during the storage of electronic cigarette can be reduced via the porous heating film.

In one of the embodiments, the diameter of the micropore on the porous body 120 ranges from 1 µm to 100 µm. Preferably, a volume of the micropore with a diameter ranging from 5 µm to 30 µm on the porous body 120 is 60% or more of a total volume of the micropore on the porous body 120. The porous body 120 can prevent the liquid from flowing rapidly to one side of porous heating film, so as to block the liquid. At the same time, the porous body 120 allows a slow penetration of the liquid to the area contacting the porous heating film, so as to implement the liquid conduction effect. In the illustrated embodiment, the porous body 120 has both excellent block and liquid conduction effect. The excellent block effect can prevent the porous body 120 from leaking liquid, and the excellent liquid conduction effect can prevent the electronic cigarette from burning dry.

In an embodiment, a porosity of the porous body 120 ranges from 30% to 83%. The porosity is a ratio of the volume of voids over the total volume in a porous medium. The value of the porosity can be adjusted according to the ingredients of the liquid, for example, for liquid with a higher viscosity, the porosity can be higher to ensure an excellent liquid conduction effect.

Additionally, in an embodiment, the porous heating film is made of metal. Furthermore, in an embodiment, the porous heating film is made of one of titanium, nickel, or nickel-chromium. A thickness of the porous heating film ranges from 0.5 µm to 1.5 µm, preferably, the thickness of the porous heating film ranges from 0.8 µm to 1 µm, and a diameter of a micropore on the porous heating film ranges from 5 µm to 30 µm.

The porous heating film can be formed on the porous body 120 via a vapor deposition method, so as to ensure a certain thickness and a porous shape of the porous heating film. Since the main micropores on the porous body 120 have a greater diameter than the thickness of the porous heating film, forming the porous heating film on the porous body 120 via vapor deposition method will not block the micropores on the porous body 120, and thus directly form the porous heating film. Specifically, in an embodiment, the vapor deposition method includes chemical vapor deposition method and physical vapor deposition method, and the physical vapor deposition method includes evaporation and sputtering.

In the illustrated embodiment, the porous body 120 can be made of porous ceramics, which is chemically stable and will not react with the liquid. Also, since the porous ceramics is resistant to high temperature, it cannot be affected by the heating from the porous heating film. The porous ceramic is also an insulator which cannot be electrically coupled to the porous heating film, thus the manufacturing process is simplified and the cost is reduced. In alternative embodiments, the porous body 120 can be made of porous glass, porous plastic, porous metal or other material that can form a porous structure. If the porous body 120 is made of a material with a lower temperature resistance such as porous plastic, a heat insulating material layer can be formed before forming the porous heating film on the porous body 120. If the porous body 120 is made of a conductive material such as metal, an insulating layer can be formed before forming the porous heating film on the porous body 120, for example, the surface of the porous metal is oxidation treated.

The different technical features of the above embodiments can have various combinations which are not described for the purpose of brevity. Nevertheless, to the extent the combining of the different technical features do not conflict with each other, all such combinations must be regarded as being within the scope of the disclosure.

The previously described implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall within the protection scope of the present disclosure. Therefore, the protection scope of the present disclosure shall be subject to the protection scope of the claims.

What is claimed is:

1. An atomizer of an electronic cigarette, comprising:
   a main body defining an airflow channel and a liquid storage cavity isolated from each other therein; and
   an atomizing element comprising a porous body and a porous heating film; the airflow channel surrounding the atomizing element, the porous body comprising an atomizing surface and a liquid absorption surface; the atomizing surface being a plane substantially parallel to a direction of an airflow in the airflow channel, the porous heating film being formed on the atomizing surface and being capable of absorbing liquid in the liquid storage cavity;
   wherein the main body comprises a liquid reservoir and an atomizing core, the liquid storage cavity is located in the liquid reservoir, the atomizing core is located in the liquid storage cavity; the atomizing element and the airflow channel are both located in the atomizing core, the atomizing core defines a connecting hole, the liquid absorption surface is located on the connecting hole, and the liquid absorption surface absorbs the liquid in the liquid storage cavity via the connecting hole.

2. The atomizer of the electronic cigarette according to claim 1, wherein the porous body comprises two atomizing surfaces that are oppositely arranged; and/or two liquid absorption surfaces that are oppositely arranged.

3. The atomizer of the electronic cigarette according to claim 1, wherein the atomizing core comprises an outer tube, an inner tube, and a sealing gasket, the outer tube is sleeved on the inner tube, and an intake channel is formed between the outer tube and the inner tube; the atomizing element and the airflow channel are both located in the inner tube; the intake channel is in communication with an end of the airflow channel; the connecting hole comprises a first connecting hole and a second connecting hole, the first connecting hole is located in the outer tube, the second connecting hole is located in the inner tube, and the first connecting hole is corresponding to the second connecting hole; the sealing gasket is located between the inner tube and the outer tube, and the sealing gasket surrounds the first connecting hole and/or the second connecting hole, such that intake channel is isolated from the first connecting hole and the second connecting hole.

4. The atomizer of the electronic cigarette according to claim 3, wherein the porous body comprises a integrally connected main part and a protruding portion, the atomizing surface is located on the main part, the liquid absorption surface is located on the protruding portion away from the main part; a side wall of the inner tube defines a latching groove, the protruding portion is latched in the latching groove, at least part of the latching groove forms the second connecting hole, and the sealing gasket surrounds the protruding portion.

5. The atomizer of the electronic cigarette according to claim 3, wherein the main body further comprises:
a mouthpiece comprising a mouth portion and a shielding portion, wherein the mouth portion defines a outlet channel in communication with another end of the airflow channel; the shielding portion is fixed to the mouth portion and shielding portion defines an adjusting opening; and
a connecting sleeve connected to the outer tube, wherein the connecting sleeve is sleeved on the mouthpiece and is rotatably connected to the mouthpiece; the connecting sleeve defines an air inlet in communication with the intake channel, the shielding portion is capable of covering the inlet, and the adjusting opening corresponds to the air inlet, a coincident area of the adjusting opening and the air inlet is adjustable by rotating the mouthpiece.

6. The atomizer of the electronic cigarette according to claim 5, wherein the air inlet is an elongated hole extending along a circumferential direction of the connecting sleeve.

7. The atomizer of the electronic cigarette according to claim 5, wherein the adjusting opening is a notch defined on an edge of the shielding portion away from the mouth portion.

8. The atomizer of the electronic cigarette according to claim 5, wherein the mouthpiece further comprises a connecting portion located between the mouth portion and the shielding portion, the connecting sleeve is sleeved on the connecting portion, and the mouthpiece is rotatably connected to the connecting sleeve via the connecting portion.

9. The atomizer of the electronic cigarette according to claim 5, wherein the atomizing core further comprises a connecting tube sleeved on the outer tube, an end of the connecting tube is connected to the liquid reservoir, and another end of the connecting tube is connected to the connecting sleeve.

10. The atomizer of the electronic cigarette according to claim 5, wherein the atomizing core further comprises an air tube, an end of the air tube is connected to the inner tube, and another end of the air tube is connected to the mouthpiece.

11. The atomizer of the electronic cigarette according to claim 1, wherein a diameter of a micropore on the porous heating file is less than a diameter of a micropore on the porous body.

12. The atomizer of the electronic cigarette according to claim 1, wherein the diameter of the micropore on the porous body ranges from 1 μm to 100 μm.

13. The atomizer of the electronic cigarette according to claim 1, wherein a volume of a micropore with a diameter ranging from 5 μm to 30 μm on the porous body is 60% or more of a total volume of the micropore on the porous body.

14. The atomizer of the electronic cigarette according to claim 1, wherein a porosity of the porous body ranges from 30% to 83%.

15. The atomizer of the electronic cigarette according to claim 1, wherein the porous heating film is made of metal, a thickness of the porous heating film ranges from 0.5 μm to 1.5 μm, and a diameter of a micropore on the porous heating film ranges from 5 μm to 30 μm.

16. The atomizer of the electronic cigarette according to claim 1, wherein the porous heating film is made of titanium, nickel, or nickel-chromium, the thickness of the porous heating film ranges from 0.8 μm to 1 μm.

17. The atomizer of the electronic cigarette according to claim 1, wherein the porous heating film is formed on the porous body via a vapor deposition method.

18. The atomizer of the electronic cigarette according to claim 1, wherein a diameter of a micropore on the porous body is greater than a thickness of the porous heating film.

19. The atomizer of the electronic cigarette according to claim 1, further comprising a battery device that is electrically coupled to the atomizer and is configured to power the atomizer.

* * * * *